(12) United States Patent
Medoff

(10) Patent No.: US 8,287,543 B2
(45) Date of Patent: Oct. 16, 2012

(54) FRACTURE FIXATION SYSTEM INCLUDING BUTTRESS PIN AND POST WASHER

(75) Inventor: Robert J. Medoff, Kailua, HI (US)

(73) Assignees: Robert J. Medoff, Kailua, HI (US); Lars G. Tellman, Falsterbo (SE); David Medoff, Valencia, CA (US)

( * ) Notice: Subject to any disclaimer, the term of this patent is extended or adjusted under 35 U.S.C. 154(b) by 888 days.

(21) Appl. No.: 10/821,643

(22) Filed: Apr. 9, 2004

(65) Prior Publication Data
US 2005/0010228 A1 Jan. 13, 2005

Related U.S. Application Data

(60) Provisional application No. 60/461,807, filed on Apr. 10, 2003.

(51) Int. Cl.
| A61B 17/56 | (2006.01) |
| A61B 17/58 | (2006.01) |
| A61B 17/82 | (2006.01) |
| A61B 17/64 | (2006.01) |
| A61B 17/84 | (2006.01) |
| A61F 2/30  | (2006.01) |

(52) U.S. Cl. ............................. 606/74; 606/75
(58) Field of Classification Search .............. 606/96, 606/74, 75, 69, 280–299, 902–906, 59, 329–330; 411/240, 530; 132/280; 24/3.12, 374
See application file for complete search history.

(56) References Cited

U.S. PATENT DOCUMENTS

| 565,255 | A | * | 8/1896 | Belden ........................ 132/281 |
| 1,315,926 | A | * | 9/1919 | Gaspar ........................ 132/280 |
| 2,031,484 | A | * | 2/1936 | Interrante ................... 132/281 |
| 3,826,024 | A | * | 7/1974 | Petersen ....................... 37/458 |
| 3,939,828 | A | * | 2/1976 | Mohr et al. .................. 606/72 |
| 4,658,822 | A | * | 4/1987 | Kees, Jr. ..................... 606/158 |
| 4,838,254 | A | * | 6/1989 | Gauthier ..................... 606/75 |
| 4,852,558 | A | * | 8/1989 | Outerbridge ................ 606/75 |
| 5,108,399 | A | * | 4/1992 | Eitenmuller et al. ........ 606/77 |
| 5,662,655 | A | * | 9/1997 | Laboureau et al. .......... 606/75 |
| 5,697,934 | A | * | 12/1997 | Huebner .................... 606/103 |
| 5,709,682 | A | * | 1/1998 | Medoff ...................... 606/60 |
| 5,779,707 | A | * | 7/1998 | Bertholet et al. ........... 606/75 |

(Continued)

FOREIGN PATENT DOCUMENTS

EP 0693272 A1 * 1/1996

(Continued)

*Primary Examiner* — Kevin T Truong
*Assistant Examiner* — David Bates
(74) *Attorney, Agent, or Firm* — Ladas & Parry LLP

(57) ABSTRACT

A fracture fixation system, particularly for a fracture at the distal end of the radius, in which a buttress pin is secured to a stable bone fragment by a bone screw and washer, and distal ends of the buttress pin are bent out of the plane of the buttress pin to engage and support a distal bone fragment. The legs of the buttress pin are spaced apart more narrowly at a U-shaped bend of the buttress pin where the buttress pin can be engaged by a conventional washer and bone screw and more widely where the bent ends engage the distal bone fragment. The washer has tabs for counter bearing against the legs to prevent spinning of the washer when the bone screw is installed. The washer can also support a fixation element which can be engaged in the distal fragment to provide additional support therefor.

36 Claims, 7 Drawing Sheets

U.S. PATENT DOCUMENTS

| | | | |
|---|---|---|---|
| 5,853,414 A * | 12/1998 | Groiso | 606/75 |
| 5,947,999 A * | 9/1999 | Groiso | 606/219 |
| 6,168,596 B1 * | 1/2001 | Wellisz et al. | 606/69 |
| 6,190,389 B1 * | 2/2001 | Wellisz et al. | 606/69 |
| 6,302,884 B1 * | 10/2001 | Wellisz et al. | 606/69 |
| 7,037,308 B2 * | 5/2006 | Medoff | 606/319 |

FOREIGN PATENT DOCUMENTS

FR 2562416 * 4/1984

* cited by examiner

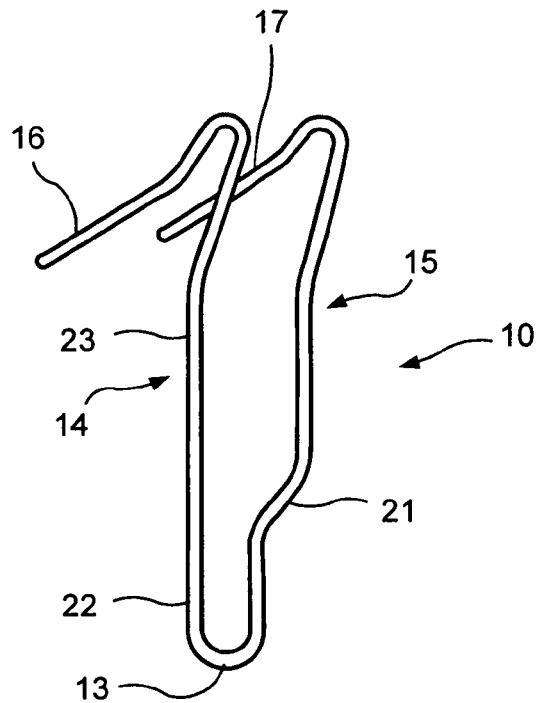
FIG. 3
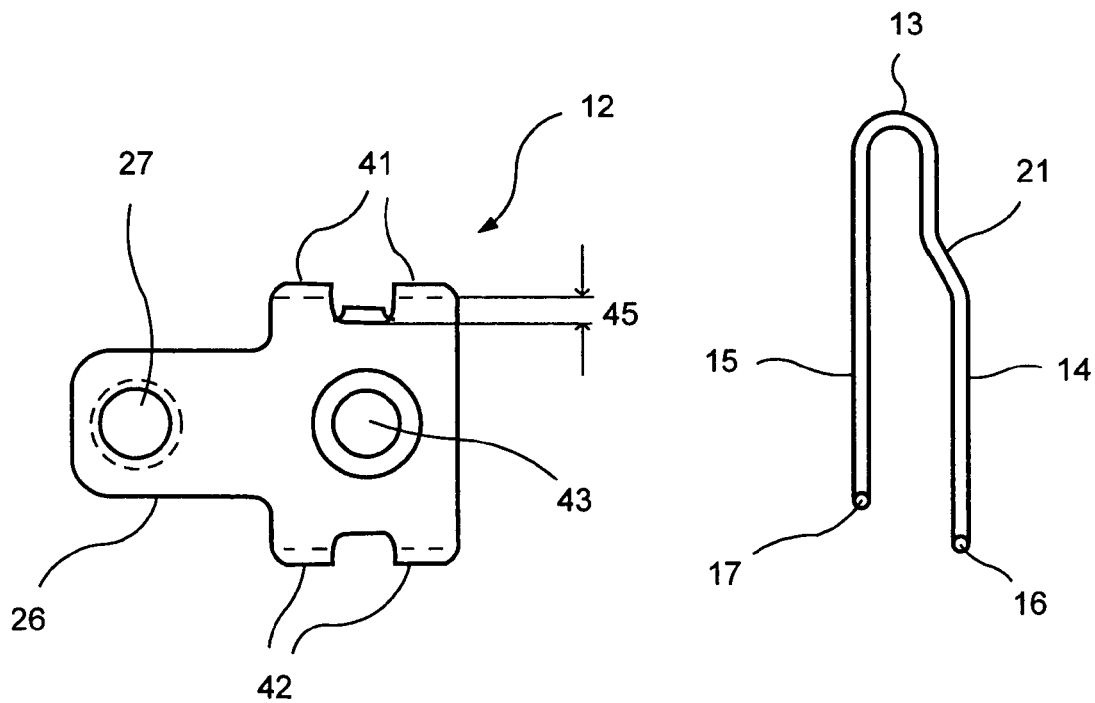
FIG. 4
FIG. 5

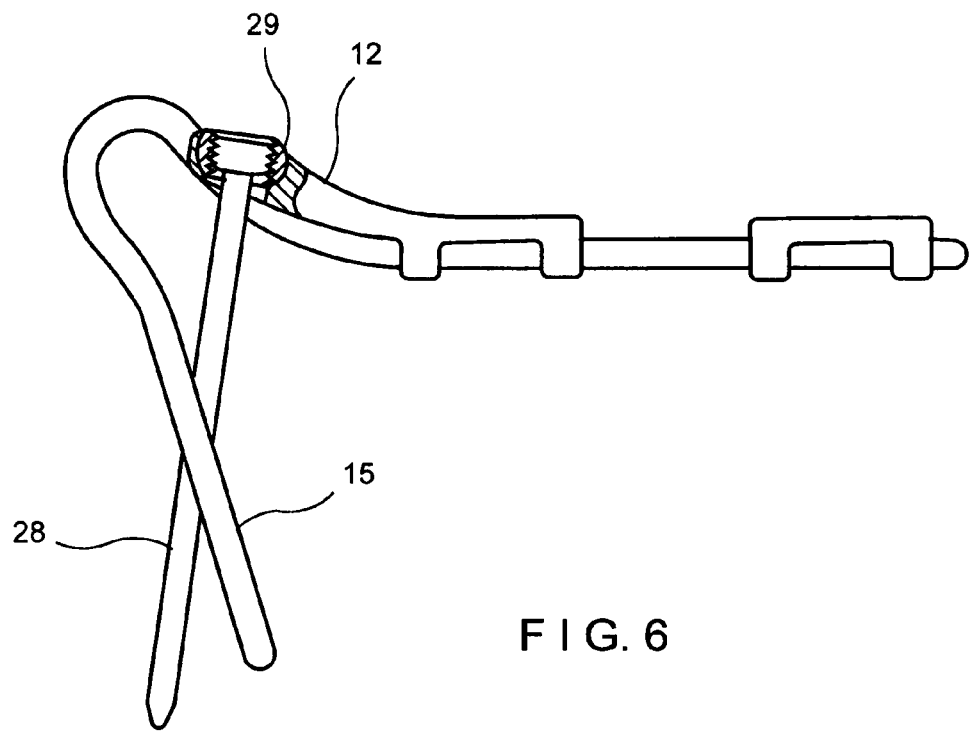
F I G. 6
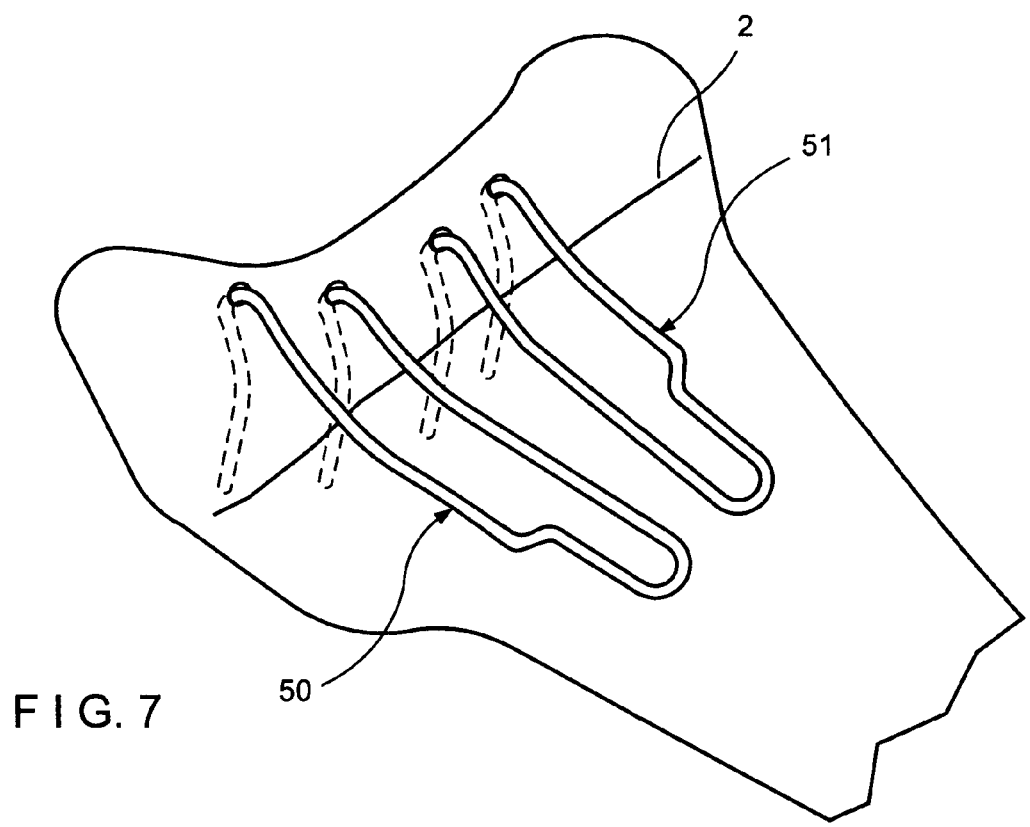
F I G. 7

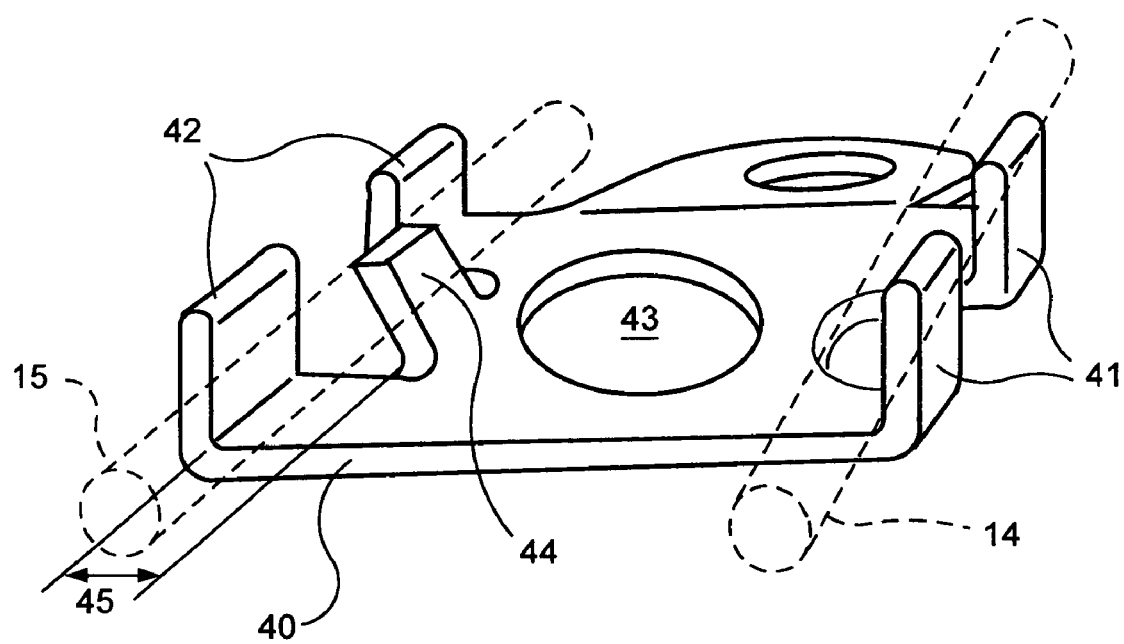
F I G. 10

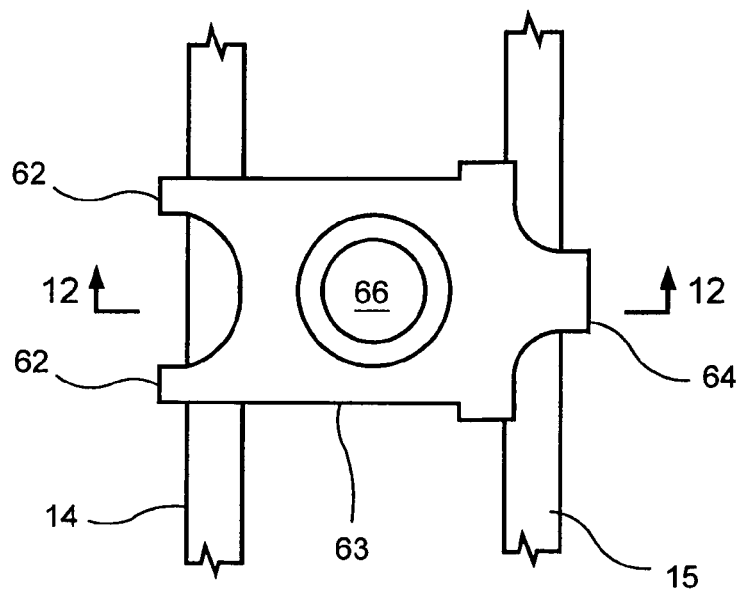
F I G. 11
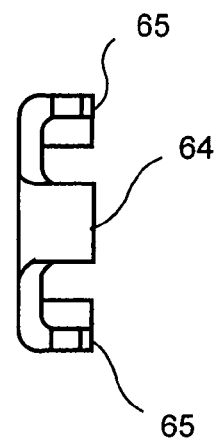
F I G. 14
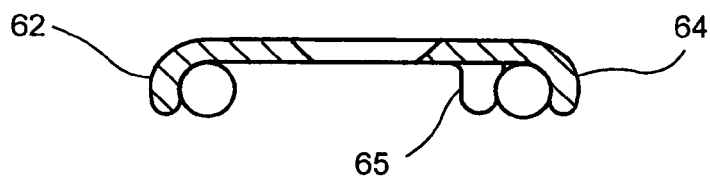
F I G. 12
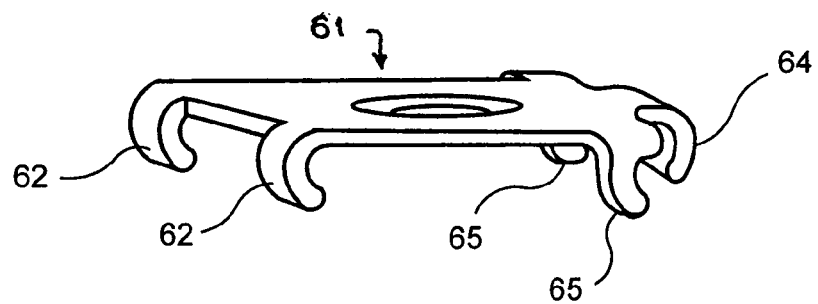
F I G. 13

FRACTURE FIXATION SYSTEM INCLUDING BUTTRESS PIN AND POST WASHER

This application claims the benefit of U.S. Provisional Application(s) No(s).: 60/461,807 filed Apr. 10, 2003 and incorporates the same by reference.

FIELD OF THE INVENTION

The invention relates to improvements in implants for fixation of fractured bones.

More particularly, the invention relates to implants having a buttress element such as a buttress pin and a washer for securing the buttress element to the bone.

The invention further relates to a method of fracture fixation utilizing a buttress pin and a securing washer.

BACKGROUND

Buttress pins are implants that are used for fixation of fractured bones. The buttress pin has a base which is usually 'U' shaped and the pin is fixed to the stable bone fragment with a bone screw and washer. At the opposite end, the buttress pin has two legs that extend out of the plane of the base of the implant. These legs are often used to penetrate an unstable bone fragment, allowing it to be manipulated into appropriate position much like a joystick. Once the fragment is manipulated into position, the base of the implant is secured proximally with the bone screw and washer. These implants have been described in my previous patents U.S. Pat. Nos. 5,709,682 and 6,113,603. Currently, however, buttress pins are only made with the legs separated at a fixed distance throughout the length of the buttress pin. In addition, existing buttress pin designs all have both legs penetrating the distal fragment in a position located at an equal distance from the 'U' shaped bend at the base of the buttress pin.

In some circumstances, such as fixation of the volar surface of the radius, the straight 'U' shaped buttress pin design with the legs spaced at an equal distance from the 'U' shaped bend is not the ideal configuration since this bone is wider distally than it is proximally. Hence, a buttress pin configuration having a separation of the legs that is wide enough to spread the support out in the distal fragment creates the situation that the implant (or pair of implants if two are used) is too wide to fit proximally. If the leg spacing is narrowed to allow one or two side by side implants proximally, the spread of the fixation legs distally is not wide enough and is inadequate for good fixation of the unstable, distal fragment. In addition, since the articular surface of the bone is not perpendicular to the long axis of the bone shaft but is at an angle or inclination, one leg of the buttress pin is often either too far distally or not far enough. Moreover, attempting to bend the pin to accommodate these deficiencies often results in changing the axis of the leg into a divergent position, compromising fixation.

Fixation of these buttress pins to the bone to reduce the fracture also poses a number of problems.

Surgeons may have to manipulate two wire implants into position while holding a small fragment, and at the same time drill and measure a hole and then place a screw and washer over the implant to secure it to the bone. In addition, since most buttress pins have two legs that extend from its 'U' shaped base, the surgeon is limited to two points of fixation for each wire implant used.

Another major technical difficulty in placement of wire forms buttress pins is to keep the washer from spinning around during insertion of the bone screw. Most washers have projecting tabs or lugs on each side thereof to capture the wire. However, these tabs spin over the wire and make it extremely awkward and time-consuming to correct the position of the washer.

Another limitation of buttress pins in general that are used to buttress curved articular fragments is that the legs of the buttress pin (or the posts of a buttress plate) that are used to buttress the articular fragment are, for the most part linear and predominantly oriented along a single axis. Since the articular surface is curved and the legs of the buttressing element are predominantly straight, there is only a single point of contact between the apex of the subchondral bone of the curved articular surface with the nearly straight leg of the buttressing element. In some cases, the buttressing element is nearly perpendicular to the long axis of the bone shaft whereby the curved articular surface has little stability to dorsal or volar migration. If, on the other hand, the buttressing element is inclined dorsally or volarly, a free articular fragment will tend to migrate along the path of least resistance to the side volarly or dorsally where there is no support.

Furthermore, plates that provide buttressing elements which are oriented at different angles are forced to fix the relative position of the multiple buttressing elements or posts to fixed locations as they enter the plate. However, since the individual osseous anatomy may be variable, the optimal relative location of two or more buttressing elements may differ from case to case. In this situation, buttress plates in which the entry locations of the posts or pegs through the plate are fixed to a specific relative location to one another cannot compensate for variations in bone morphology.

SUMMARY OF THE INVENTION

An object of the invention is to provide a fracture fixation system comprised of one or more buttress pins and associated washer and bone screw, which overcomes the deficiencies of the known constructions as explained above.

Another object of the invention is to provide a combination of the buttress pin and the washer which facilitates installation of the buttress pin and provides favorable buttressing of the distal bone fragment.

Another object of the invention is to provide means on the washer to maintain its position on the buttress pin before and during installation of the bone screw.

Yet another object of the invention is to enable the washer to provide another point of fixation in addition to that provided by the buttress pin. This additional point of fixation can be achieved by a fixation element installed through the washer.

In addition, since the position of the washer may be adjusted proximally or distally before it is fixed to the proximal bone fragment, the relative position of the fixation element that is connected to the washer can be adjusted relative to the legs of the buttress pin.

Another object of the invention is to allow the washer to be physically connected to the buttress pin to keep the washer from falling off while the bone screw is inserted, yet allow adjustment in the position of the washer proximally or distally to the ideal location. This eliminates the necessity of manually holding the washer in position while the sequence of drilling the screw hole, measuring the hole depth, and inserting the screw is performed and simplifies the surgical procedure for the surgeon.

Another object of the invention is to overcomes the problem of supporting a curved surface with an essentially linear buttressing element, by providing both a volarly and dorsally inclined orientation to the buttressing elements, thereby, providing a central location of stability for the apex of the curved articular surface.

In accordance with the invention, the washer is fabricated to allow it to attach directly to at least one leg of the buttress pin, preventing it from falling off or spinning around when the bone screw is installed. In this respect, at least three extension tabs extend from the sides of the washer. Two of these tabs extend on one side of the legs at the buttress pin, the third tab being positioned on an opposite side of one leg. The tabs are curved or inclined to each other so that the leg can be snapped into position between the tabs. The fixation is loose enough to allow the washer to be slid to the desired position, but prevents the washer from dislodging off of the leg of the buttress pin and thus prevents the washer from falling off the buttress pin or spinning underneath the legs.

The washer can be supplied with a crimping instrument which allows the three tabs to be crimped over the wire before being implanted into the body. This simplifies quality control of the washers by allowing the surgeon to crimp the tabs to get the desired amount of fixation on the legs of the buttress pin.

In further accordance with the invention, in addition to the tabs placed on the sides of the washer to capture the legs of the buttress pin, an additional tab(s) is provided on the distal and/or proximal end of the washer to provide additional constraint to the washer against spinning as the bone screw is inserted, as well as provide for capturing the end of the 'U' shaped base of the buttress pin.

In further accordance with the invention, the washer is modified to allow an additional point of purchase into the unstable bone fragment by providing a projection on the washer extended toward the unstable bone fragment for placing a central post or screw through the washer between the legs of the buttress pin into the unstable bone fragment. This post or screw may be unthreaded or threaded, and is installed at an angle relative to the legs of the buttress pin and/or the surface of the washer. Additionally, the head of the post or screw may be threaded to directly couple it to the washer and prevent angulation of the post or screw in the hole in the washer.

In a variation, the directional axis of the post or screw is in an opposite orientation than the directional axis of the legs of the buttress pin. For instance, for support of the curved articular surface of the distal radius, the orientation of the legs of the buttress pin may be in dorsal inclination and the orientation of the post inserted in the washer may be in volar orientation. As seen laterally, these two buttressing elements would be oriented on opposite sides of a vertical line, creating a central area of stability in the center where the axes of the two elements cross each other. Just as a screw head will naturally seat in the center of a beveled hole, the articular surface will seek the position of most stability in the vicinity of the apex of the articular curve.

In further accordance with the invention, the washer can be extending proximally to allow additional bone screw fixation to the stable bone fragment. This extension may be beyond the end of the buttress pin.

In further accordance with the invention, the washer is made wide enough to capture two buttress pins placed side by side.

In further accordance with the invention, the washer can be provided with a bearing in the hole for receiving the post or screw thus providing adjustment for the angle at which the post or screw is to be inserted into the unstable bone fragment.

In accordance with the invention, the buttress pin is formed from a continuous bent wire having a first end bent into a predominantly 'U' shape, and opposite legs extending from the U-shaped bend to a second end at which the legs are bent out of the plane of the U-shaped bend in order to penetrate a bone fragment. The spacing of the legs between the first end and the second end differs in at least two locations.

In further accordance with the invention, the position of the two legs at the second end is at different distances from the first end.

In further accordance with the invention, the length of the two legs from the first end are different from one another.

In further accordance with the invention, the spacing between the legs is reduced in a region proximate th U-shaped bend as compared to the spacing in the region of the second end.

In further accordance with the invention, the legs are parallel to one another in the respective regions.

As previously stated, the fixation washer is provided for securing the buttress pin to a bone, the washer comprising at least three tabs. The tabs extend at least at one side of the washer such that at least two tabs are positioned on one side of the legs of the buttress pin and at least one further tab is positioned on the other side of one of the legs. The washer contains at least one hole for securing the washer to the bone with a bone screw.

In further accordance with the invention, the two tabs and the further tab are inclined toward each other in order to capture the leg of the buttress pin and prevent it from dislodging therefrom.

The tabs can be straight or curved and a crimping tool can be used to crimp the tabs on the legs of the buttress pin.

In further accordance with the invention, the washer has at least one hole for securing the washer to a stable bone fragment, and at least one additional hole for adding one or more additional fixation element directly through the washer into the unstable bone fragment.

In further accordance with the invention, the additional hole is obliquely oriented to the surface of the washer.

BRIEF DESCRIPTION OF THE FIGURES OF THE DRAWING

FIG. 3 is a perspective view of a buttress pin of the fracture fixation system.

FIG. 4 is a top plan view of a washer of the fracture fixation system.

FIG. 5 is a top view of another embodiment of the buttress pin.

FIG. 6 is a modification of FIG. 2.

FIG. 7 diagrammatically illustrates of two buttress pins installed in side by side relation prior to installation of the washers and bone screws.

FIG. 10 is a perspective view of the washer as seen from below.

FIG. 11 is a top plan view of another embodiment of the washer engaged with the legs of the buttress pin.

FIG. 12 is a sectional view taken along line 12-12 in FIG. 11.

FIG. 13 is a perspective view of the embodiment of the washer shown in FIG. 11 without the buttress pin.

FIG. 14 is a side view of the washer in FIG. 11.

DETAILED DESCRIPTION

Figure 1:
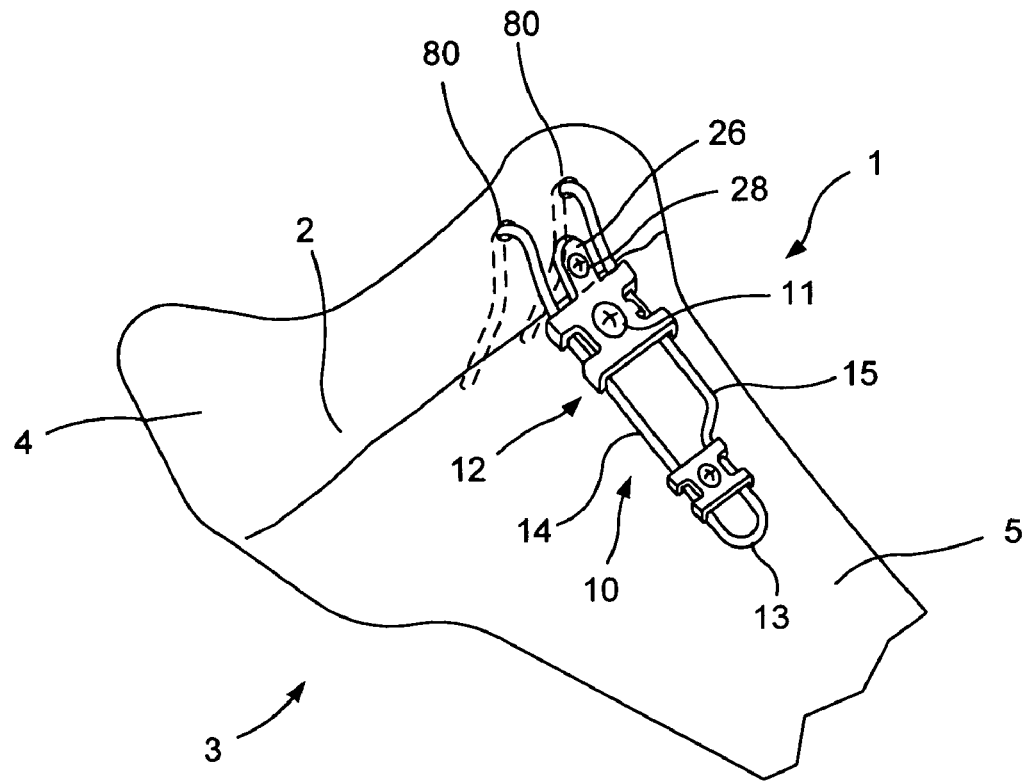
FIG. 1 diagrammatically illustrates a fracture fixation system according to the invention applied to a fractured bone.

FIG. 1 shows a fracture fixation system 1 adapted for fixation of a fracture 2 of a bone 3. The bone 3 will be considered herein as the distal end of the radius of the wrist but the fracture fixation system 1 is adapted for fixation of fractures of other bones, such as the distal end of the fibula, the medial malleolus of the ankle and the distal end of the ulna, as well known to those skilled in the art.

The fracture 2 of the bone 3 produces an unstable distal bone fragment 4 and a stable bone fragment 5. The fixation system 1 provides fixation of the fracture as will become evident from the description which follows.

The fracture fixation system 1 comprises a wire element 10 serving as a buttress pin which engages and positions the unstable bone fragment 4 to reduce the fracture. The buttress pin 10 is secured in position by a bone screw 11 that is screwed into the stable bone fragment 5. The bone screw 11 engages the buttress pin 10 through the intermediary of a washer 12.

FIG. 3 illustrates the buttress pin 10, and as seen therefrom, the buttress pin is formed from a wire element having a U-shaped bend 13 from which legs 14 and 15 extend. At their distal ends, the legs 14 and 15 are bent out of the plane of the U-shaped bend 13 to form bent ends 16 and 17 respectively which form an L-shape for the legs 14 and 15 as seen in FIG. 3 and wherein bent ends 16 and 17 form radial buttressing elements adapted to bear against bone surface 18 (FIG. 2) and provide support for the articular surface 19 at the articular distal end of the bone fragment 2 of the radius.

As seen in FIG. 3, leg 14 of the buttress pin 10 is straight and leg 15 has an outward bend 21 to form an offset beyond which the spacing between legs 14 and 15 is increased. Thus, legs 14 and 15 are parallel and are spaced apart in a region 22 proximate the U-shaped bend 13 at a distance which is less than the space between the parallel legs 14 and 15 beyond the outward bend 21 in a distal region 23. This allows the buttress pin 10 to be secured by a conventional washer 24 (FIG. 2) at the proximal end 22 of the buttress pin 10 where the bone 3 is narrower than at the distal end 19, whereas the bent ends 16 and 17 at the distal end of the buttress pin 10 can be spaced further apart to provide more effective support at the wider end of surface 18 of distal bone fragment 4. The offset bend 21 has been shown on leg 15 in FIG. 3. However, the offset bend 21 is provided in either leg 14 or leg 15 depending on whether the buttress pin is installed on the volar or ulnar side (see FIG. 7).

Furthermore, since the surface 18 of the bone fragment 4 is not perpendicular to the longitudinal axis of the bone and is not planar, the leg 14 can be made longer than the leg 15 to position leg 15 more deeply into the bone in the distal direction to make contact with the more distant part of the surface 18.

The bent end 16 is made longer than bent end 17 to facilitate its entry into a pre-drilled hole 80 in the distal bone fragment 4 before inserting the tip of bent end 17 into its respective pre-drilled hole.

Figure 2:
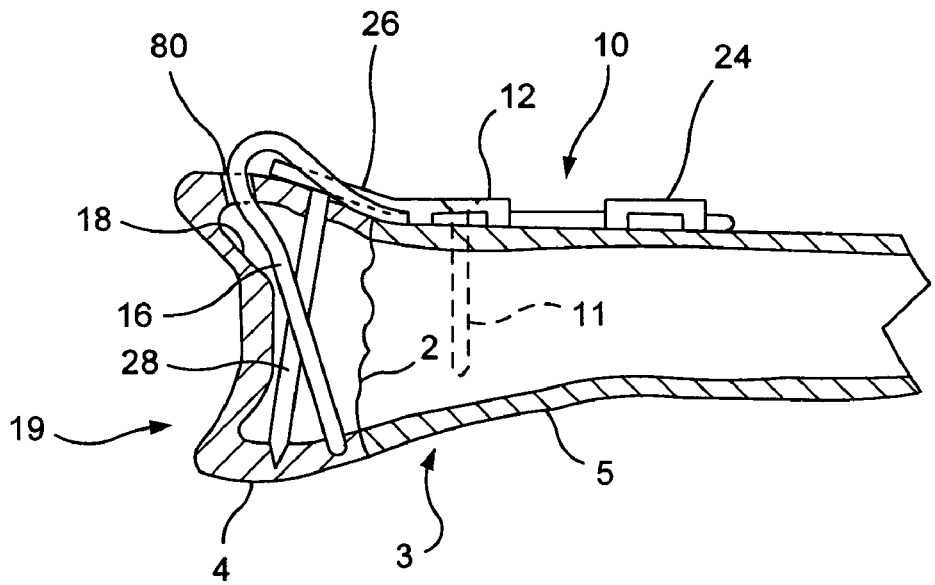
FIG. 2 is a longitudinal sectional view through the fracture fixation system of FIG. 1.

The washer 12 is provided with a projection 26 extending in a distal direction on the surface of bone 3. The projection 26 is inclined upwards as seen in FIG. 2 to follow the shape of the bone 3. The projection 26 is provided with a hole 27 (FIG. 3) to receive a post or peg 28 which penetrates into the bone fragment 4 as shown in FIG. 2 to provide further bearing support for surface 18 of the bone fragment 4. The bent ends 16, 17 of the buttress pin 10 and the post 28 are inclined relative to one another in opposite directions and bear against the bone surface 18 to oppose migration of the unstable bone fragment. In particular, it is seen that the bent ends 16, 17 are inclined distally with respect to the vertical whereas the post 27 is inclined proximally.

The post 28 can have a smooth or threaded distal end depending on the desired degree of engagement in the bone fragment 4.

The hole 27 in projection 26 can incorporate a split bearing 29 which is initially rotatable in the hole 27 to allow adjustment of the angle at which the post 28 is inserted into the bone. The post can be widened at its head 30 which then acts to expand the bearing as the post is advanced therein to lock the bearing 29 in the hole 27 and fix the angle of the post.

The head 30 of the post can be threaded as shown in FIG. 5 to engage a threaded bore in the bearing so that as the post 28 is threaded into the bearing 29 it also becomes threadably engaged with the bearing.

The washer can also be provided with a projection (not shown) extending in a proximal direction to receive a bone screw to provide additional fixation to the proximal bone fragment 5.

Figure 8:
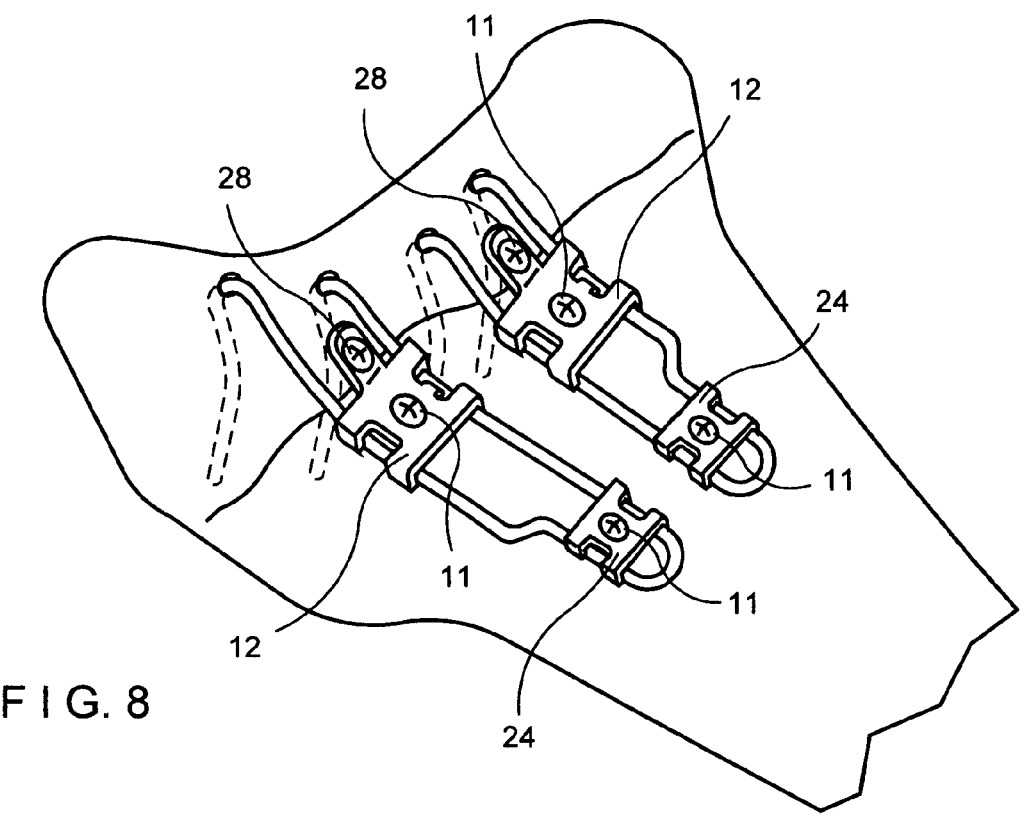
FIG. 8 is similar to FIG. 7 but shows the buttress pins after installation of the washers and screws.

Referring next to the washer 12, particularly as shown in FIGS. 4 and 8, the washer comprises a body 40 at the side edges of which respective pairs of tabs 41 and 42 are bent out of the plane of the body. A hole 43 is provided in the body 40 for insertion of the bone screw 11. The pair of tabs 41 and 42 are laterally spaced apart to engage the outer surfaces of legs 14 and 15 in the region 23 where the legs are more widely spaced apart. In order to prevent slippage of the washer 12 from the legs of the buttress pin and spinning of the washer as the bone screw 11 is screwed into the bone fragment 4, a further tab 44 is bent out of the plane of the body 40 to face the pair of tabs 42 and define a clearance space 45 therebetween in which the leg 15 is received. The tab 44 is bent slightly towards tabs 42 so that the clearance space 45 is slightly less than the diameter of leg 15. The tab 44 has sufficient flexibility to enable the leg 15 to be snap-engaged into clearance space 45 whereafter the washer 12 can be slidably moved along the legs of the buttress pin 10 for proper positioning of the bone screw 11 and the post 28 for insertion into the bone fragment 4. After the washer 12 has been moved to its desire position, the bone screw 11 is screwed into the bone fragment 4. During this procedure, the tabs 42 bear against the outer surface of leg 15 while the tab 44 bears against the inner surface of leg 15 to apply a counter pressure on leg 15 as the screw is turned to prevent relative rotation of the washer 12 with respect to the buttress pin 10.

After the bone screw 11 has been seated, the post 28 is installed through the hole 27 in projection 26 into the bone fragment 4.

Instead of being flat as shown in FIG. 10, tab 44 can be curved to conform to the shape of leg 15 so as to apply the counter bearing pressure on the leg 15 over the entire inner surface thereof when the bone screw 11 is installed.

The washer 12 can be made of metal or plastic material.

Figure 9:
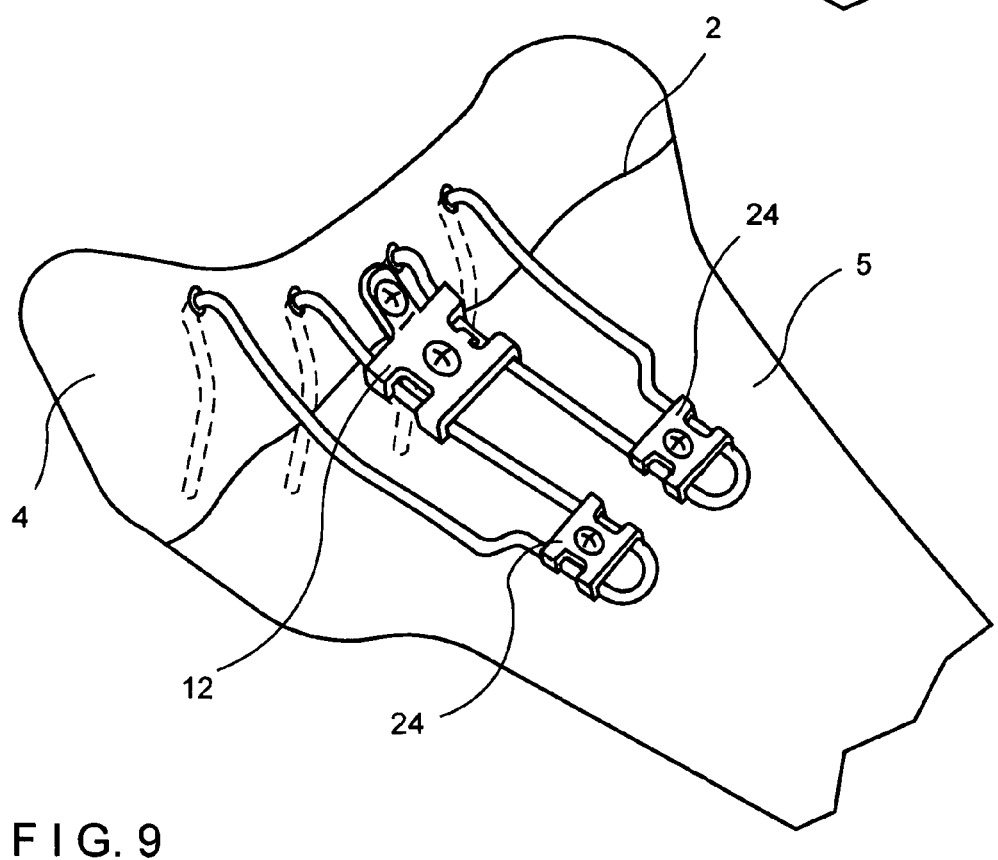
FIG. 9 is similar to FIG. 8 except that a single washer is used to secure the buttress pins to the distal fragment.

FIG. 7 shows a fracture fixation system in which two buttress pins 50, 51 are utilized for fixation of the bone fracture. The left buttress pin 50 has unequal length legs to correspond to the increased bone size whereas the right buttress pin 51 has legs of equal length. Each buttress pin can be secured with a respective washer 12, as shown in FIG. 8 but according to the invention it is advantageous if both buttress pins are secured by a common washer 12 as shown in FIG. 9. A single post 28 is installed in the bone fragment 4. Conventional washers 24 and bone screws 11 are utilized to secure the buttress pins 50 and 51 at their narrow regions 22 to the proximal bone fragment 5. As an alternative, the washer 12 can be made wide enough to engage the outer legs of buttress pins 50, 51, instead of the adjacent inner legs and two or more projections 27 with respective fixation elements 28 can be provided.

FIGS. 11-14 show a modified version of the washer 61 in which two tabs 62 are formed on one side of body 63 and one tab 64 is formed on the opposite side of the body 63. The tabs 62 and 64 engage the outer facing surfaces of legs 14, 15 of the buttress pin. Two additional outwardly facing tabs 65 are bent from the body 63 to engage he inwardly facing surface of the leg 15 to provide counter pressure on the leg 15 in opposition to tab 64 to prevent relative rotation of the washer 61 when the bone screw is inserted through hole 66 into the bone. In this embodiment, the projection with the hole for the installation of the post is absent.

Figure 15:
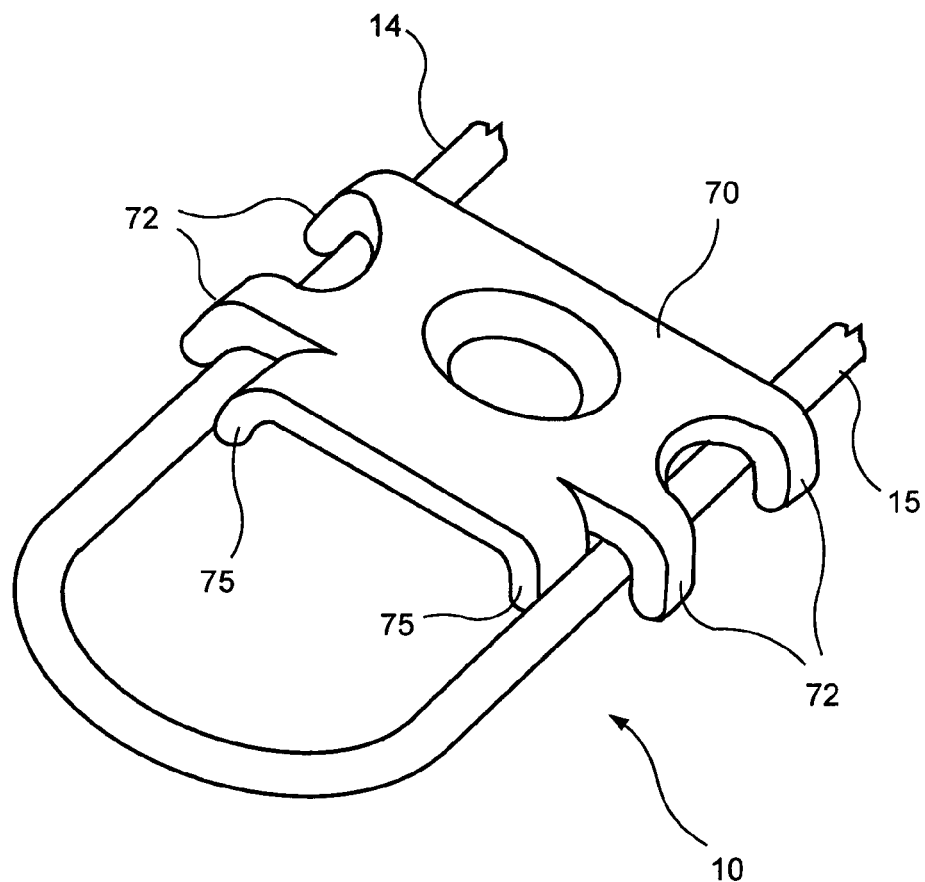
FIG. 15 is a perspective view of another embodiment of the washer engaged with the legs of the buttress pin.
Figure 16:
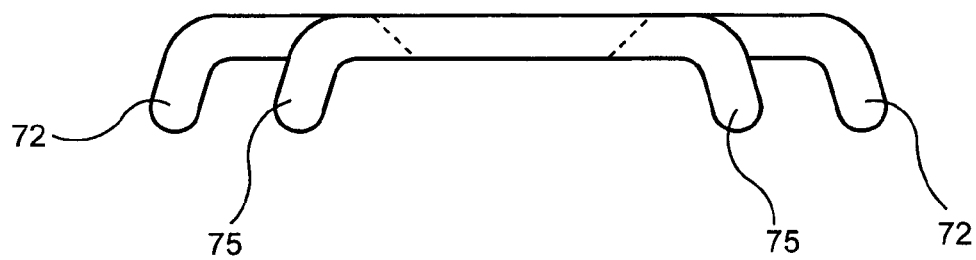
FIG. 16 is a side elevational view of the washer of FIG. 15 alone.

FIGS. 15 and 16 show another version of the washer 71. In this version, two pairs of tabs 72, 73 are formed at the side edges of body 74 for engaging outwardly facing surfaces of legs 14 and 15. A pair of additional tabs 75 extend from the body 74 to engage the inwardly facing surfaces of legs 14 and 15 to provide the counter pressure on the washer when the bone screw is installed and thereby prevent the relative rotation of the washer with respect to the buttress pin 10. This version of the washer, similar to that in FIGS. 11-14, does not have a projection to receive a post and can be used in replacement of the conventional washer 24 shown in FIG. 1. All of the disclosed versions of the washers can be provided with the projection for the post or not.

The method for installation of the buttress pin for fracture fixation of the bone is as follows.

Two pilot holes 80 (FIG. 1) are formed in the distal fragment 3 approximately 1 mm past the ridge that marks the end of the flare of the volar surface of the distal radius. The pilot holes are separated by a distance that approximates the distance between the downwardly bent ends 17, 18 of the legs of the buttress pin 10. The pilot holes are oriented with respect to the central axis of the teardrop of the volar rim.

The washer 12 is then snapped onto one leg of the buttress pin and is slid distally towards the bent ends. The legs of the pin are cut to the desired length leaving the ulnar side (bent end 17) slightly longer for ease of insertion of the bent ends into the pilot holes. The bent ends of the buttress pin are then installed and the buttress pin is turned so that the legs are placed along the central axis of the teardrop.

The washer is then slidably adjusted to the appropriate location on the buttress pin and the bone screw 11 is installed to secure the washer and underlying buttress pin to the proximal bone fragment 5. The configuration of the tabs on the washer holds the washer in place when the bone screw is threadably advanced into the bone to prevent the washer from spinning. The snap-on feature of the washer provides reliable attachment and retention thereof on the buttress pin and allows it to be manipulated into position easily as contrasted with conventional washers which have no attachment to the buttress pin during installation.

Thereafter, the post is installed in the distal fragment to complete the fixation of the fracture.

Additional conventional washers 24 can be installed as necessary to obtain secure fixation of the buttress pin to the bone.

Although the invention is disclosed with reference to particular embodiments thereof, it will become apparent to those skilled in the art that numerous modifications and variations can be made which will fall within the scope and spirit of the invention as defined by the attached claims.

The invention claimed is:

1. An implant for stabilization of an unstable bone fragment in relation to a stable bone fragment, said implant comprising an offset buttress pin comprising an elongated single wire element having opposite ends and extending longitudinally between said opposite ends, a U-shaped bend at one of said ends of the wire element and opposite legs extending longitudinally from the U-shaped bend toward the opposite end of the elongated wire element, said opposite legs each having a first portion that lies in a plane of the U-shaped bend and a second portion at the opposite end of the wire element that lies outside the plane of the U-shaped bend, said legs being bent downwardly from said first portion to form in said second portion predominantly linear distal ends at said opposite end of the wire element which depend from the first portion and form an angle with respect to the plane of the U-shaped bend, such that each leg of the wire element is predominantly of L shape, each of said distal ends being constructed and arranged to penetrate radially into the unstable bone fragment and are of sufficient length to constitute means for engaging in and buttressing the unstable bone fragment against transverse displacement towards the stable bone fragment, the arrangement of the legs being such as to satisfy at least one of two conditions in which 1) said first portion of said legs having a first region in proximity to said U-shaped bend and a second region in proximity to said second portion, said legs being spaced apart in said first region at a distance which is different from the spacing of the legs in said second region so that the distal ends of the legs are spaced apart by a distance different from the spacing of the legs in said first region and 2) the legs have a length from the U-shaped bend to the distal ends which are unequal.

2. The implant of claim 1, wherein the legs extend parallel to one another in said first and second regions.

3. The implant of claim 2, wherein one of said legs is bent outwardly in a direction away from the other of the legs to form a step separating the first and second regions.

4. The implant of claim 1, wherein said opposite legs extending from the U-shaped bend are of equal length.

5. The implant of claim 1, wherein said opposite legs extending from the U-shaped bend are of unequal length.

6. The implant of claim 1, wherein the lengths of said bent distal ends of said second portion of the legs are unequal.

7. The implant of claim 1, wherein one of said legs of the wire element is straight and the other leg has a bend therein to define first and second sections in which the legs are parallel and spaced apart and wherein the spacing between the legs in the first section is less than the spacing between the legs in the second section.

8. The implant of claim 1, wherein said wire element has a round cross-section.

9. The implant of claim 1 further comprising a fixation washer for securing the wire element to a bone in proximity to said first region.

10. The implant as claimed in claim 9, comprising a second buttress pin adjacent to the first said buttress pin, said washer engaging one said leg of each of said first and second buttress pins for securing said first and second buttress pins to the stable bone fragment.

11. The implant as claimed in claim 9, said fixation washer comprising a body for lying on the wire element said body having a hole for passage therethrough of a bone screw adapted to secure the washer and the underlying wire element to said stable bone fragment, and means on said body of the washer for applying a pressure on the legs of the wire element to oppose rotation of the washer and slippage of the washer from said legs when the bone screw is turned for engagement in the stable fragment.

12. The implant as claimed in claim 9, wherein said washer includes a projection extending lengthwise between the legs of the wire element, said projection having a second hole for passage therethrough of a fixation element adapted to penetrate into said unstable bone fragment.

13. The implant as claimed in claim 12, wherein said fixation element and the legs of said second portion of the wire element extend at an angle relative to one another.

14. The implant as claimed in claim 12, said fixation washer comprising a body for lying on the wire element said body being associated with a second hole longitudinally spaced from the first hole in a position for insertion of a fixation element adapted for being secured to the unstable bone fragment.

15. The implant as claimed in claim 14, wherein said fixation element comprises a screw adapted for insertion into the unstable fragment of the bone.

16. The implant as claimed in claim 14, wherein said fixation element comprises a post adapted for threaded engagement in the unstable fragment of the bone.

17. The implant as claimed in claim 16, wherein said post has a threaded head and said second hole is threaded for threaded engagement by said threaded head of the post.

18. The implant as claimed in claim 16, wherein said fixation element includes a portion adapted for buttressing the unstable bone fragment at an articulate surface thereof, said legs of said second portion being adapted for buttressing the articulate surface, said portion of the fixation element and the bent distal ends of said legs of said second portion extending at different angles with respect to the articulate surface.

19. The implant as claimed in claim 18, wherein said portion of the fixation element and said bent distal ends of said legs of said second portion of the wire element extend in opposite directions of inclination.

20. The implant as claimed in claim 1, wherein said second hole extends obliquely in said projection.

21. The implant as claimed in claim 20, wherein said fixation element is secured in said projection by an expandible bearing in said second hole.

22. The implant as claimed in claim 12, wherein the second hole causes the fixation element to be angularly offset with respect of the wire element.

23. The implant as claimed in claim 12, wherein the angular offset of the fixation element and the legs of the second portion of the wire element are adapted to produce separate contact regions with an articulate portion of the bone fragment.

24. The implant of claim 1, wherein said single wire element consists of said U-shaped bend and said opposite legs extending therefrom.

25. The implant of claim 24, wherein said bent distal ends of said legs of said second portion are shaped to engage internally against and provide support for an articular surface of the bone fragment.

26. The implant of claim 1, wherein bends which join said first and second portions are curved.

27. The implant of claim 1, wherein said distal ends of the second portion of the legs of the wire element are shaped and arranged to be adapted to enter respective holes in the unstable bone fragment.

28. The implant of claim 27, wherein one of said distal ends of said legs of said second portion is longer than the other of said distal ends of said legs of the second portion to enable tips of said end of said legs enter said holes one after the other.

29. The implant of claim 1, wherein the distal ends of the legs of the second portion are inclined distally with respect to the plane of the U-shaped bend.

30. The implant of claim 1, wherein said legs of said second portion are dimensioned to be adapted to penetrate into the unstable bone fragment.

31. The implant of claim 1, wherein distal ends of said second portion have lengths adapted to be substantially equal to the thickness of the bone fragment.

32. The implant as claimed in claim 1, wherein said legs extend predominantly longitudinally from said U-shaped bend to said bent distal ends.

33. The implant as claimed in claim 1 wherein said U-shaped bend has a curved base and said legs of said first portion extend directly from said curved base.

34. The implant as claimed in claim 1 wherein the downwardly bent distal ends of said second portion form terminal ends of the buttress pin that face downwardly from said first portion to penetrate an upper surface of the unstable bone fragment from above.

35. The implant as claimed in claim 34 wherein the downwardly bent distal ends of said second portion are positioned to extend crosswise of the unstable bone.

36. The implant as claimed in claim 35 wherein said distal ends of said second portion extend predominantly perpendicular to the legs of said first portion.

* * * * *